(12) United States Patent
Cossard

(10) Patent No.: US 6,295,335 B1
(45) Date of Patent: Sep. 25, 2001

(54) RADIOGRAPHIC CONTROL OF AN OBJECT HAVING A CRYSTAL LATTICE

(75) Inventor: Serge Georges Guy Cossard, Argenteuil (FR)

(73) Assignee: Societe Nationale d'Etude et de Construction de Moteurs d'Aviation "Snecma", Paris (FR)

(*) Notice: Subject to any disclaimer, the term of this patent is extended or adjusted under 35 U.S.C. 154(b) by 0 days.

(21) Appl. No.: 09/600,872

(22) PCT Filed: Dec. 15, 1999

(86) PCT No.: PCT/FR99/03142

§ 371 Date: Aug. 11, 2000

§ 102(e) Date: Aug. 11, 2000

(87) PCT Pub. No.: WO00/36404

PCT Pub. Date: Jun. 22, 2000

(30) Foreign Application Priority Data

Dec. 17, 1998 (FR) .................................................. 98/15914

(51) Int. Cl.[7] ...................................................... H05G 1/26
(52) U.S. Cl. ............................ 378/98.12; 378/70; 378/71
(58) Field of Search .................................... 378/98.12, 73, 378/70, 71, 77

(56) References Cited

U.S. PATENT DOCUMENTS 5,136,624 * 8/1992 Schneider et al. ...................... 378/73
5,987,095 * 11/1999 Chapman et al. ...................... 378/70

* cited by examiner

Primary Examiner—Robert H. Kim
Assistant Examiner—Hoon K. Song
(74) Attorney, Agent, or Firm—Oblon, Spivak, McClelland, Maier & Neustadt, P.C.

(57) ABSTRACT

The invention relates to the inspection of an object (105) by radiography, this object possessing a crystal lattice. It consists of submitting the object (105) to electromagnetic radiation (103) to obtain a radiographic image of the object on receptor means (114) the radiographic image obtained, corresponding to one exposure, being a composed image resulting from a relative displacement of the object (105) which makes it possible to substantially reproduce the object while significantly attenuating the parasitic elements produced by diffraction of the electromagnetic radiation on the crystal lattice of the object.

15 Claims, 4 Drawing Sheets

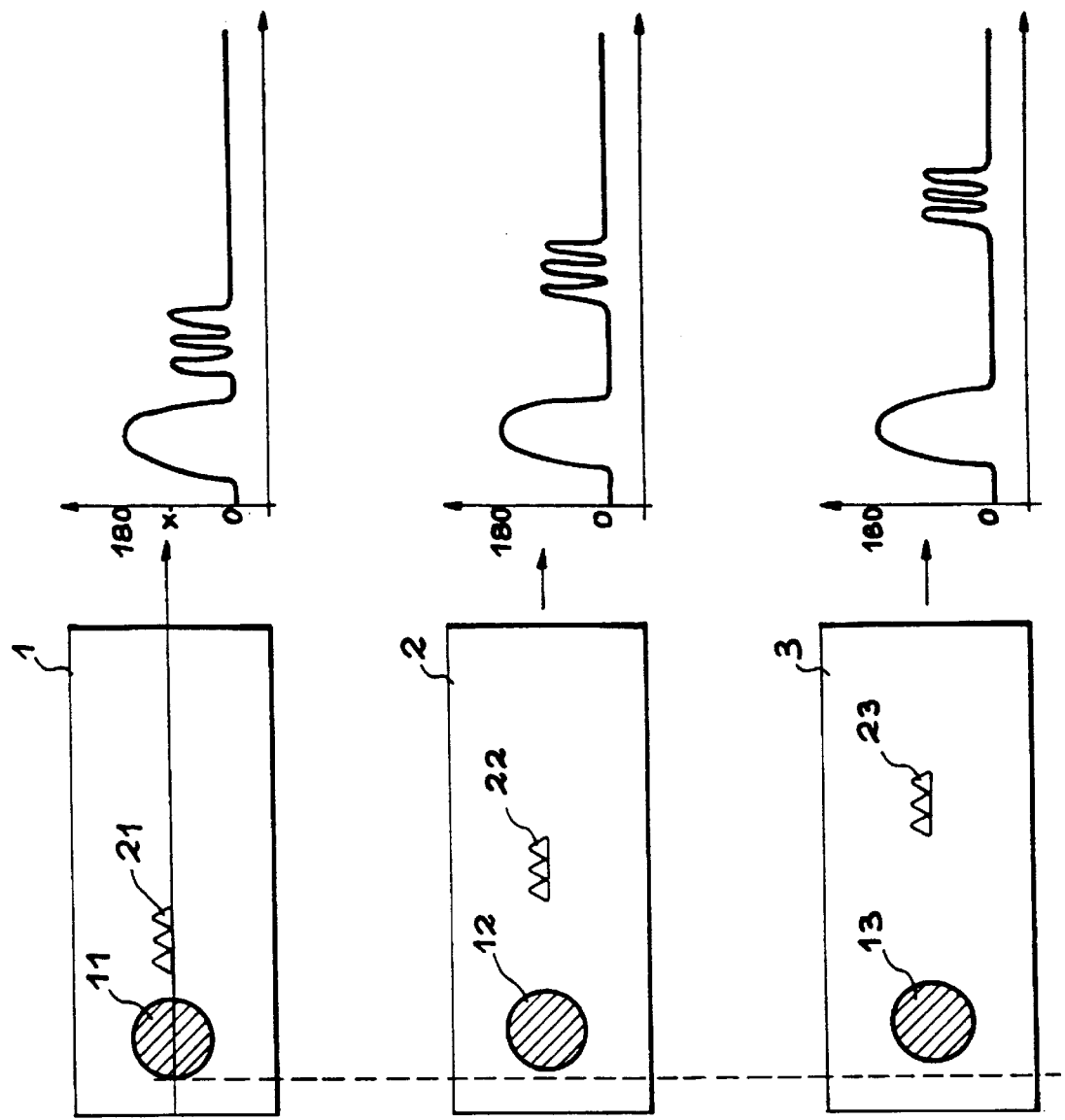

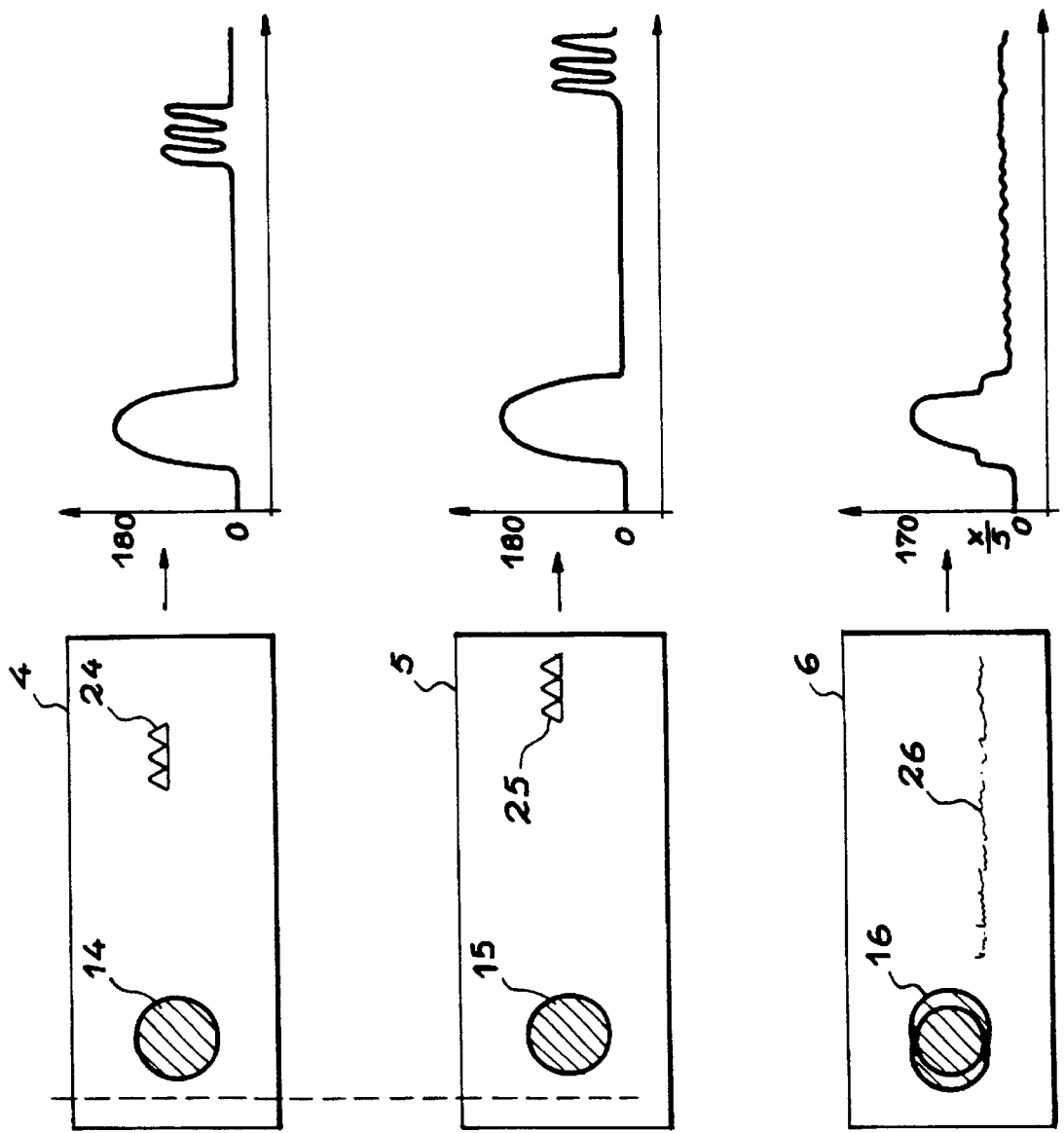

RADIOGRAPHIC CONTROL OF AN OBJECT HAVING A CRYSTAL LATTICE

BACKGROUND OF THE INVENTION

1. Field of the Invention

The present invention relates to the inspection by radiography of an object possessing a crystal lattice.

2. Discussion of the Background

Non-destructive tests (also called non-destructive testing) make it possible to provide information about the condition of a part or a structure without any resulting changes which could prejudice their ulterior use. Thus it is possible to detect internal defects which cannot be revealed during a superficial inspection. Internal defects in a part can vary greatly: shape defects, dimension defects, the presence of inclusions, cracks, etc.

The principle of detecting a defect, according to non-destructive testing, consists of exciting the defect and collecting its response. Thus a part to be inspected can be submitted to a flux of ionising radiation and, by studying the transmitted flux, one can detect an eventual defect thanks to the perturbation of the flux it introduces.

By submitting the part to be inspected to very short wavelength electromagnetic radiation (X or $\gamma$), it is possible to collect intensity modulations of the beam transmitted under the form of an image on an appropriate receptor (for example a film). The radiography (X or $\gamma$) uses a detector in real time which is an element or an assembly of elements transforming photons (X or $\gamma$) into an electric signal which at the outlet delivers either an analogue signal, or digital data. Besides these X and $\gamma$ radiography procedures, there is also neutrography which uses neutron beams.

According to the radioscopy (X or $\gamma$) procedure the radiographic image is captured, by a fluorescent screen for example, and produces an optical image which can be observed directly and in real time.

Contrary to a simple radiography, tomography makes it possible to provide information about the complete morphology of a defect thanks to several exposures taken under different angles.

The field of application of industrial radiography is very vast and concerns parts of all kinds.

However, when an exposure is made under the classic conditions of radiography or radioscopy, if the part being inspected possesses a crystal lattice, this irradiated crystal lattice emits radiations of the same wavelength as the electromagnetic radiation crossing through it. This secondary radiation provokes diffraction according to the Bragg equation. This diffraction causes parasitic radiation, creating confusion between the defects present in the part and the parasitic indications. These parasitic radiations can also mask the indications being looked for.

SUMMARY OF THE INVENTION

The invention has been designed to remedy the inconvenience mentioned above by attenuating the influence of this diffraction.

Thus the aim of the invention is an inspection procedure of an object by radiography, said object possessing a crystal lattice, consisting of submitting said object to electromagnetic radiation in order to obtain a radiographic image of said object on receptor means, characterised in that the radiographic image obtained, corresponding to an exposure, is a composed image resulting from a relative displacement of said object while significantly attenuating the parasitic elements produced by diffraction of the electromagnetic radiation on the crystal lattice of the object.

If the radiographic image is a radioscopy, the relative displacement of the object can be due either to a displacement in the direction of the electromagnetic radiation, or to a displacement of the said object. In this case, the composed image can be an averaged image resulting from the average of several images obtained respectively following several elementary displacements constituting said relative displacement.

If the radiographic image is a single exposure on film, the relative displacement of the object can come either from a change in direction of the electromagnetic radiation, or from a displacement of the film.

If the radiographic image is obtained by tomography and its acquisition carried out by line by line reading, the composed image can be constituted of odd lines corresponding to a first elementary displacement and even lines corresponding to a second elementary displacement.

Advantageously, the first elementary displacement corresponds to a displacement of the object from a first angle defined relative to the direction of the electromagnetic radiation, of the same amplitude as the first defined angle but with inverse sign.

A further aim of the invention is a device for inspection of an object by radiography, said object possessing a crystal lattice, comprising means of emission of electromagnetic radiation able to form a radiographic image, means of support of the object allowing said object to be submitted to said electromagnetic radiation, receptor means of the response of the object to said electromagnetic radiation and supplying a radiographic image of said object, characterised in that means are envisaged for provoking a relative displacement of said object, during the formation of a radiographic image corresponding to an exposure, so as to make it possible to obtain a composed image reproducing to a considerable extent said object while significantly attenuating the parasitic elements produced by diffraction of the electromagnetic radiation on the crystal lattice of the object.

If the device operates in radioscopy, the means provoking the relative displacement of the object can be means of displacement of the direction of electromagnetic radiation or can be constituted by the means of support of the object. The receptor means can then be means making it possible to deliver an averaged image resulting from the average of several images obtained respectively following several elementary displacements constituting said relative displacement.

If the device provides a radiographic image under the form of a single exposure on film, the means provoking the relative displacement of the object can be means for changing the direction of the electromagnetic radiation or means for displacing the film.

If the device operates in tomography, the acquisition of the radiographic image being carried out by line by line reading, the receptor means can include means for constituting said composed image from odd lines corresponding to a first elementary displacement and even lines corresponding to a second elementary displacement. The means provoking the relative displacement of the object can be constituted by the means of support of the object which ensure the first elementary displacement thanks to a displacement of the object by a first angle defined relative to the direction of the electromagnetic radiation, and which ensure the second elementary displacement thanks to a displacement of the object by a second angle defined relative to the direction of the electromagnetic radiation, the first and second elementary displacements being of the same amplitudes but of inverse signs.

BRIEF DESCRIPTION OF THE DRAWINGS

The invention will be better understood and other advantages and particularities will appear upon reading the following description, given as a non-restrictive example, accompanied by the drawings in the appendices among which:

FIGS. 3 to 7 represent five radiographic images of an object possessing a crystal lattice, taken after the relative displacements of the object and intended to form a composed radiographic image according to the present invention, each of the five radiographic images being associated with a cut in luminance of the radiographic signal received;

FIG. 8 represents the averaged radiographic image obtained from the radiographic images represented in FIGS. 3 to 7, this averaged image being associated with a cut in luminance of its radiographic signal;

DESCRIPTION OF THE PREFERRED EMBODIMENTS

In order to reduce the influence of objectionable radiation, one provokes, as mentioned above, a relative displacement of the object inspected in relation to the electromagnetic radiation or in relation to the receptor organ. The relative displacement can be a displacement of the object itself, a displacement of the source emitting the electromagnetic radiation or yet again a displacement of the receptor organ.

Figure 1:
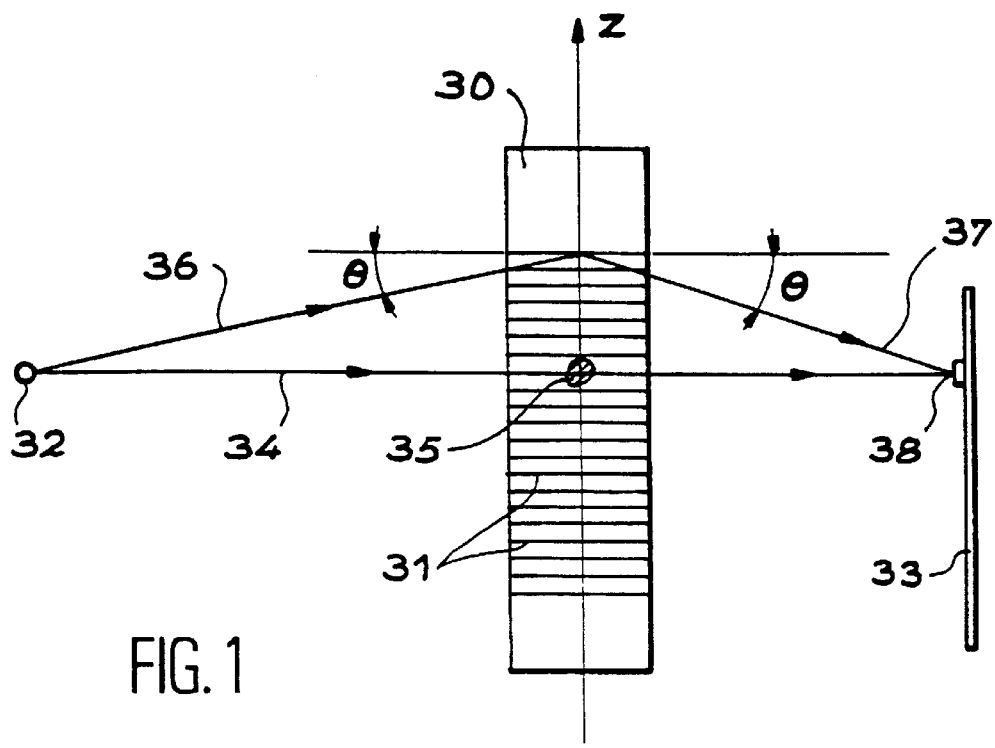
FIGS. 1 and 2 illustrate the principle applied in the present invention.
Figure 2:
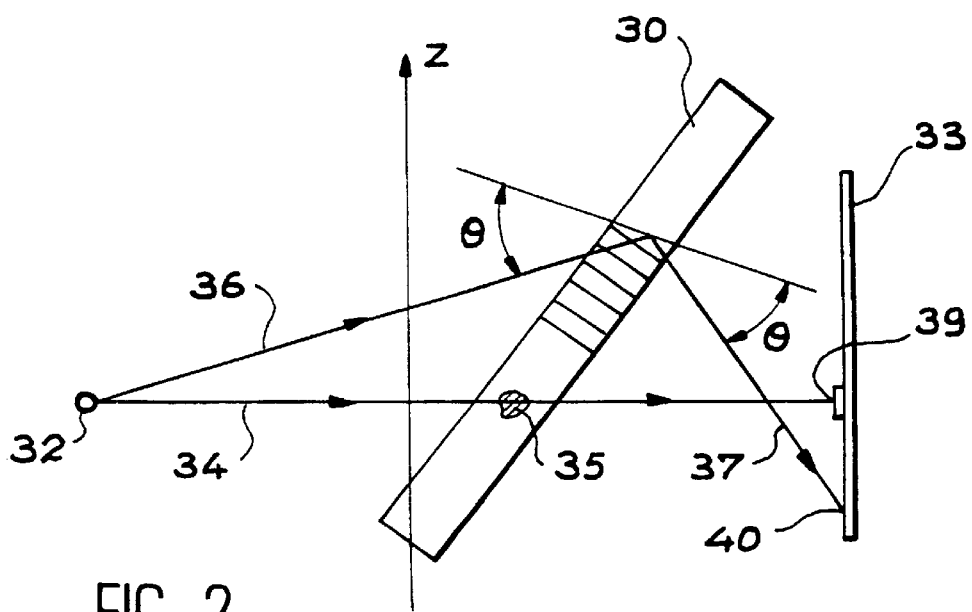

FIGS. 1 and 2 illustrate the principle applied in the present invention. An object 30 is represented in schematic fashion, possessing a crystal lattice and whose crystal planes are shown under reference 31. The direction of the crystal planes 31 was chosen perpendicular to an axis z the same as the longitudinal axis of the object 30. The object 30 is submitted to electromagnetic radiation supplied by an appropriate source 32. After crossing the object 30, the electromagnetic radiation reaches a detector whose plane carries the reference 33. Two rays of electromagnetic radiation have been represented: ray 34 which crosses the object 30 at the place where the latter has a defect 35, and ray 36 which arrives on the crystal plane according to the Bragg angle θ. In response to the ray 36, the crystal lattice emits a ray 37 under conditions corresponding to the Bragg equation:

$$2d \sin \theta = n\lambda$$

d being the distance between the crystal planes of the object,

λ being the radiation wavelength emitted belonging to the emission spectrum of the source 32, n being a whole number equal to or greater than 1.

Rays 34 and 36 were chosen such that the ray 34 transmitted and the ray 37 diffracted form on the plane of the detector 33 an image combining the image of the defect and the diffraction pattern.

On FIG. 2, the object 30 has been inclined relative to the axis z. As a result of this there is a differentiation of the images received on the plane of the detector 33. A ray 34 transmitted crossing the defect produces an image of this defect 39 on the plane of the detector. A ray 36 reaching the object 30 under the condition of diffraction corresponding to the Bragg equation leads to a diffracted ray 37 producing a diffraction pattern 40 on the plane of the detector.

The displacements can consist of simple or combined movements (linear or angular) carried out at the time of taking the radiographic images, with the aid of a manipulating robot or other mechanised system.

The magnitudes of the displacements depend on the nature of the material(s) constituting the objects, the thickness of the object to undergo radiography, its type of solidification, the acceptation criteria envisaged for pronouncing compliance or not with the manufacture of the objects.

In the case of radioscopy by means of X-rays, for example, one obtains the composed image by making an average of n successive primary images. FIGS. 3 to 7 each represent a primary image obtained after successive displacements of the object. The displacements of the object are minimal. The result of this is a composed image on which a defect present in an object is detectable even if its image obtained is very slightly modified. On the other hand, the displacements however minimal, mean that the parasitic image elements due to the crystal diffraction are sufficiently separated from one image to the other so that these elements are not added together. In this case, when the average image is obtained, the parasitic image elements will be practically no longer detectable.

FIG. 3 represents a first image collected, 1, in which a defect is visible under reference 11 as well as a parasitic defect 21. The accompanying graph represents the cut in luminance of the signal received along axis x.

FIG. 4 represents a second image received, 2, after slight displacement of the object. The defect in the object is visible 12 and the parasitic defect, 22. It is to be noted that the defect in the object is visible with a very slight shift in relation to image 1, whereas the parasitic defect visible 22 cannot be superposed on the parasitic defect visible, 21. These shifts are also represented on the accompanying graph of luminance.

FIG. 5 represents a third image collected, 3, after another displacement of the object, of the same amplitude as the preceding displacement. The defect in the object is visible 13 and the parasitic defect, 23.

FIG. 6 represents a fourth image collected, 4, after another displacement of the object, of the same amplitude as the preceding displacement. The defect in the object is visible 14 and the parasitic defect, 24.

FIG. 7 represents a fifth image collected, 5, after a final displacement of the object, of the same amplitude as the preceding displacement. The defect in the object is visible 15 and the parasitic defect, 25.

As FIG. 8 shows, the averaged image 6, presented to the controller by radioscopy, is the sum of the primary images obtained divided by five. The definitive image 16 of the defect is slightly altered while the resulting parasitic defect 26 is very attenuated in relation to the initial parasitic defect.

In the case of classic industrial radiography, the final image obtained is made from a single exposure on film. The relative displacements of the object can be obtained by displacement of the X-ray emission tube or by displacement of the film during exposure.

In the case of tomography, the so-called DR (Digital Radiography) system is comparable to a televised radioscopy where the receptor organ is no longer a surface but linear, to such an extent that the acquisition of the image is achieved by scanning, that is to say by reading line by line.

In this case, in order to attenuate the parasitic effect due to the crystal diffraction, one can apply the following principle:

a first sweep of n DR integrations with an odd step (1, 3, 5, 7, etc.) and a rotation of the object through a predetermined angle+α.

a second sweep of n DR integrations with an even step (2, 4, 6, 8, etc.) and a rotation of the object through a predetermined angle –α.

The final image reconstituted by interlacing the even and odd lines allows significant attenuation of the parasitic radiation.

Figure 9:
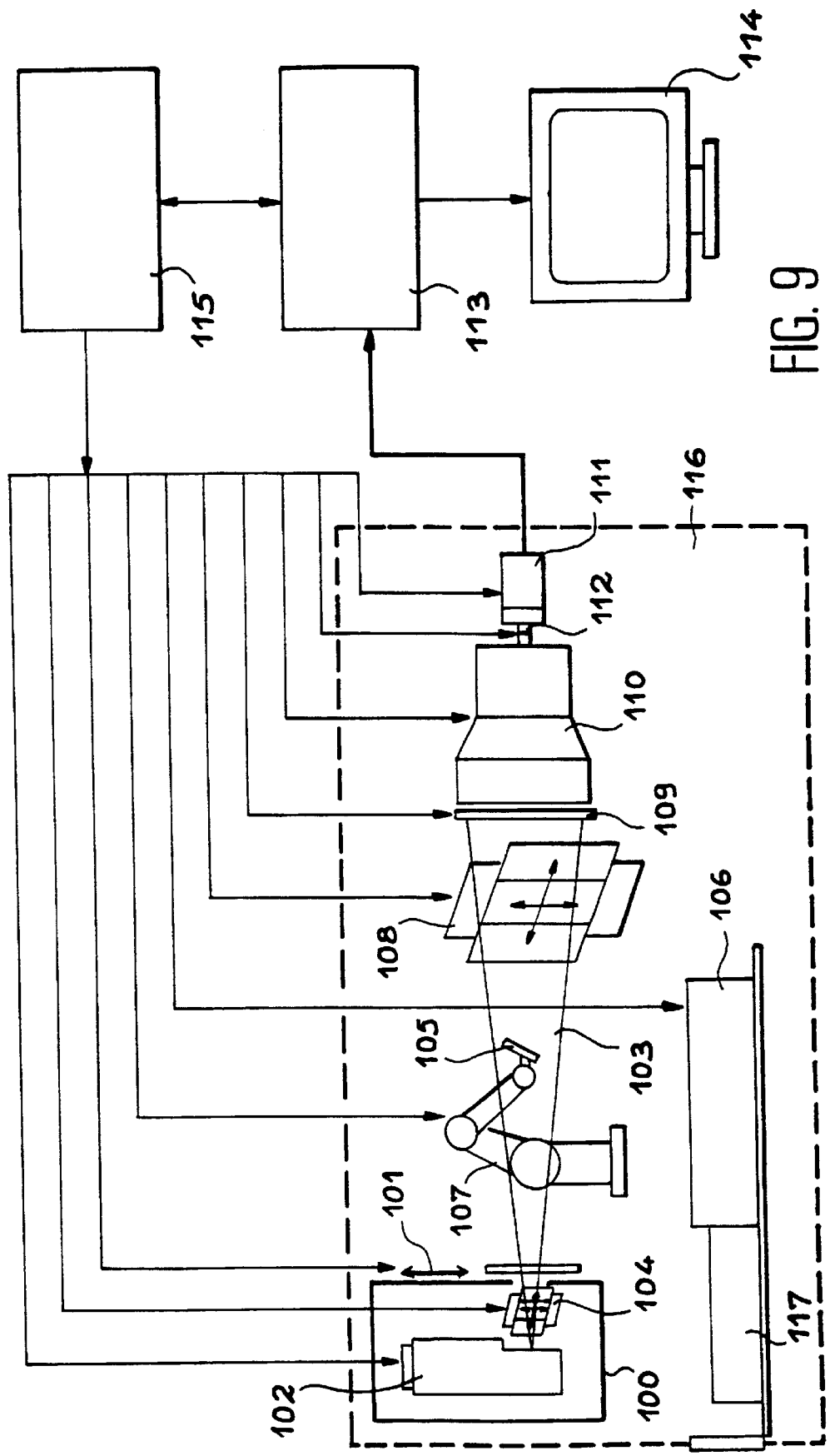
FIG. 9 is a plan of a televised radioscopy device according to the present invention.

FIG. 9 represents the plan of a televised radioscopy device applying the principle of the invention. An insulated housing 100 provided with a shutter 101 encloses an X-ray source 102, which emits rays 103 through a collimator, 104. The object to be inspected 105, initially set in a container 106, is seized by a manipulating robot 107 to be submitted to X-rays 103. The X-rays which have crossed the object 105 pass through a diaphragm with four flaps 108 and into a post-filtration element 109 to reach a brightness amplifier 110. The brightness amplifier 110 transmits the signal received to a camera 111 via a diaphragm 112. The camera 111 delivers an output signal to a unit for treating images 113 which delivers a composed image to the control screen 114 on the one hand and also communicates with a unit 115 in charge of piloting the different organs of the radioscopy device enclosed in a protective cabin 116. Once the inspection has been carried out, the inspected parts are put into a receiving container 117.

What is claimed is:

1. A procedure for inspecting an object by radiography, said object possessing a crystal lattice, consisting of submitting said object to electromagnetic radiation to obtain a radiographic image of said object on receptor means, characterised in that the radiographic image obtained, corresponding to one exposure, is a composed image resulting from a relative displacement of said object which makes it possible to reproduce to a considerable extent said object while significantly attenuating the parasitic elements produced by diffraction of electromagnetic radiation on the crystal lattice of the object.

2. An inspection procedure according to claim 1, characterised in that, the radiographic image being a radioscopy, said relative displacement of the object comes either from a displacement of the direction of electromagnetic radiation or from a displacement of said object.

3. An inspection procedure according to claim 2, characterised in that said composed image is an averaged image resulting from the average of several images obtained respectively following several elementary displacements constituting said relative displacement.

4. An inspection procedure according to claim 1, characterised in that the radiographic image being a single exposure on film, said relative displacement of the object comes either from a change in direction of the electromagnetic radiation, or from a displacement of the film.

5. An inspection procedure according to claim 1, characterised in that the radiographic image being obtained by tomography and its acquisition being carried out by line by line reading, said composed image is constituted of odd lines corresponding to a first elementary displacement and even lines corresponding to a second elementary displacement.

6. An inspection procedure according to claim 5, characterised in that the first elementary displacement corresponds to a displacement of the object by a first angle defined in relation to the direction of electromagnetic radiation, and in that the second elementary displacement corresponds to a displacement of the object by a second angle defined in relation to the direction of the electromagnetic radiation, of the same amplitude as the first defined angle but with inverse sign.

7. A device for inspecting an object by radiography, said object possessing a crystal lattice, comprising means of emission of electromagnetic radiation able to form a radiographic image, means of support for the object making it possible to submit said object to said electromagnetic radiation, receptor means (111, 113, 114) of the response of the object to said electromagnetic radiation, and supplying a radiographic image of said object, characterized in that means are envisaged for provoking a relative displacement of said object, during the formation of a radiographic image corresponding to one exposure, in order to make it possible to obtain a composed image reproducing said object to a considerable extent while significantly attenuating the parasitic elements produced by the diffraction of the electromagnetic radiation on the crystal lattice of the object.

8. An inspection device according to claim 7, characterised in that, the device operating in radioscopy, the means provoking the relative displacement of said object are means of displacement of the direction of the electromagnetic radiation.

9. An inspection device according to claim 7, characterised in that, the device operating in radioscopy, the means provoking the relative displacement of said object are constituted by the support means of the object.

10. An inspection device according to claim 8, characterised in that said receptor means are means making it possible to deliver an averaged image resulting from the average of several images obtained respectively following several elementary displacements constituting said relative displacement.

11. An inspection device according to claim 7, characterised in that, the device supplying a radiographic image under the form of a single exposure on film, the means provoking the relative displacement of said object are means for changing the direction of electromagnetic radiation.

12. An inspection device according to claim 7, characterised in that, the device supplying a radiographic image under the form of a single exposure on film, the means provoking the relative displacement of said object are means for displacing said film.

13. An inspection device according to claim 7, characterised in that, the device operating in tomography and the acquisition of the radiographic image being carried out by line by line reading, said receptor means include means for constituting said composed image from odd lines corresponding to a first elementary displacement and even lines corresponding to a second elementary displacement.

14. An inspection device according to claim 13, characterised in that the means provoking the relative displacement of said object are constituted by the means of support of the object which ensure the first elementary displacement thanks to a displacement of the object by a first angle defined relative to the direction of the electromagnetic radiation, and which ensure the secondary elementary displacement thanks to a displacement of the object by a second angle determined relative to the direction of electromagnetic radiation, the first and second elementary displacements being of the same amplitudes but of inverse signs.

15. An inspection device according to claim 9, characterized in that said receptor means are means making it possible to deliver an averaged image resulting from the average of several images obtained respectively following several elementary displacements constituting said relative displacement.

* * * * *